United States Patent [19]
LeGrow et al.

[11] Patent Number: 5,389,365
[45] Date of Patent: Feb. 14, 1995

[54] SILICONE TERPOLYMER CONTAINING WATER-IN-OIL EMULSION DERIVED FROM UNSATURATED ETHYLENE OXIDES

[75] Inventors: Gary E. LeGrow; David A. Glover, both of Midland, Mich.

[73] Assignee: Dow Corning Corporation, Midland, Mich.

[21] Appl. No.: 192,537

[22] Filed: Feb. 7, 1994

[51] Int. Cl.$^6$ .................. A61K 7/48; C08G 77/38
[52] U.S. Cl. .................. 424/78.03; 424/78.02; 424/401; 528/15; 528/25
[58] Field of Search .............. 528/15, 25; 424/401, 424/78.02, 78.03

[56] References Cited

U.S. PATENT DOCUMENTS

| | | | |
|---|---|---|---|
| 3,427,271 | 2/1969 | McKellar | 260/29.2 |
| 5,118,764 | 6/1992 | Ichinohe et al. | 528/25 |
| 5,166,295 | 11/1992 | Herzig | 528/25 |
| 5,232,693 | 8/1993 | Legrow | 424/78.37 |
| 5,262,087 | 11/1993 | Tachibana et al. | 252/309 |

*Primary Examiner*—Thurman K. Page
*Assistant Examiner*—Peter F. Kulkosky
*Attorney, Agent, or Firm*—James L. DeCesare

[57] ABSTRACT

A water-in-oil emulsion and a method of making the emulsion in which the emulsion includes 5 to 50 percent by weight of an organic oil; 44 to 94.5 percent by weight of water; and 0.5 to 5 percent by weight of a water dispersible silicone wax. The emulsion is free of organic emulsifying agents. The water dispersible silicone is a wax derived from the reaction of (i) an ≡SiH containing siloxane; (ii) a linear C30+ organic alpha-olefin; and (iii) an unsaturated ethylene oxide polymer. Emulsions having a viscosity in about 150,000 centistokes to about 200,000 centistokes are described.

6 Claims, No Drawings

SILICONE TERPOLYMER CONTAINING WATER-IN-OIL EMULSION DERIVED FROM UNSATURATED ETHYLENE OXIDES

BACKGROUND OF THE INVENTION

This invention is directed to a silicone terpolymer formed from three components. The components used to produce the silicone terpolymer are (i) an ≡SiH containing siloxane, (ii) an organic alpha-olefin, and (iii) an unsaturated ethylene oxide polymer.

Silicones containing long chain organic substitution in the molecule which are waxes are not water dispersible. Silicones containing polyether substitution in the molecule which are water dispersible are not waxes.

The problem or dilemma to be resolved by the present invention is to make a silicone which is a water dispersible wax, and which wax can be used in the formation of water-in-oil emulsions without the need for any organic emulsifying agent. These problems are solved, according to the present invention, by forming a water dispersible silicone wax which contains in its molecule both long chain organic substitution and polyether substitution.

Such a water dispersible silicone wax is prepared by chemically combining (i) an ≡SiH containing siloxane polymer or copolymer, (ii) a high melting C30+ organic alpha-olefin, blend, or fraction, and (iii) a high melting unsaturated ethylene oxide polymer having the formula $H_2C=CH-CH_2-O(CH_2CH_2O)_xH$ in which x has a value of at least sixteen.

The softening point of a high melting C30+ organic alpha-olefin is about sixty degrees Centigrade. The softening point of a high melting unsaturated ethylene oxide polymer is about thirty-eight degrees Centigrade.

Depending upon the ratio of substitution, one skilled in the art would expect that a silicone containing in the molecule both a high melting C30+ organic group, and a high melting ethylene oxide group, would have a softening point intermediate of the softening point of a silicone containing only the high melting C30+ organic group (60° C.), and a silicone containing only the high melting ethylene oxide group (38° C.).

However, what is surprising and unexpected, is that the water dispersible silicone wax terpolymer of the present invention has a softening point higher (75° C.) than either; with a large percent of substitution by the high melting C30+ organic group (60° C.), and with a small percent of substitution by the high melting ethylene oxide group (38° C.).

Because of its unique and unexpected characteristics, the water dispersible silicone wax terpolymer of the present invention possesses a utility as a water-in-oil emulsifying agent, and it is capable of producing stable high viscosity emulsions which are free of any organic emulsifying agent. These emulsions have particular application in the personal care segment of the consumer market.

SUMMARY OF THE INVENTION

It is an object of the invention to provide a water dispersible silicone wax. It is also an object of the invention to provide a new silicone composition which has a softening point higher than would be expected of a silicone containing in the molecule a large percent of substitution by a high melting C30+ organic group, and a small percent of substitution by a high melting ethylene oxide group.

It is a further object of the invention to form water-in-oil emulsions which are free of organic emulsifying agents.

These and other features, objects, and advantages of the present invention, will become more apparent from a consideration of the following detailed description thereof.

DETAILED DESCRIPTION OF THE INVENTION

The new water dispersible silicone wax is prepared by chemically combining three components.

The first component is an ≡SiH containing siloxane polymer or copolymer. This siloxane polymer can be in the form of a linear polymethylsiloxane such as $Me_3SiO(MeHSiO)_xSiMe_3$. The siloxane can also be a linear polymethylsiloxane-polydimethylsiloxane copolymer such as $Me_3SiO(MeHSiO)_x(Me_2SiO)_ySiMe_3$ in which the different units along the main backbone chain of the copolymer have a random distribution. In both formulas, Me denotes the methyl radical, and x and y denote integers.

These siloxane polymers and copolymers are commercially available. However, in order to produce a water dispersible silicone wax according to the invention, the value of the integer x must be from twenty to about one hundred. In addition, the value of the integer y must be from one to about one hundred, with the proviso that the ratio of x/y is at least two or more.

The second component is a high melting linear C30+ organic alpha-olefin, blend, or fraction. This material is available commercially as a chemical composition with an average of twenty-four or more carbon atoms, preferably thirty carbon atoms or more. Exemplary of such commercial products is a line of alkene chemicals manufactured and marketed under the trademark GULFTENE ® by the Chevron Chemical Company, Houston, Tex. USA.

One such product is GULFTENE ® 24–28 which is an alpha-olefin fraction containing a blend of alpha-olefins with a weight distribution of mixed C22 to C30+ alkenes. This blend or fraction includes about one percent of C22 alkenes, about thirty percent of C24 alkenes, about thirty-nine percent of C26+ alkenes, about twenty percent of C28 alkenes, and about ten percent of C30+ alkenes. The average number of carbon atoms in this blend is twenty-four.

Another and more preferred product is GULFTENE ® 30+ which is an alpha-olefin fraction containing a blend of alpha-olefins with a weight distribution of mixed C28 to C30+ alkenes. This blend or fraction includes about twenty-two percent of C28 alkenes and about seventy-eight percent of C30+ alkenes. The average number of carbon atoms in this blend is thirty.

The third component is a high melting unsaturated ethylene oxide polymer having the formula $H_2C=CH-CH_2-O(CH_2CH_2O)_zH$ in which z must have a value of at least sixteen. These waxy polyether materials are commercially available. The softening point of such polyether waxes is about 28° C. when the degree of polymerization is sixteen, and reaches a maximum of about 50° C. when the degree of polymerization is twenty-eight or more.

The silicone terpolymer is made by chemically combining stoichiometric amounts of the three components in the presence of a platinum catalyst such as chloroplatinic acid. Sufficient of the ≡SiH containing siloxane polymer or copolymer is employed in order to provide a slight excess of SiH. In the first step, the siloxane polymer and the alpha-olefin fraction are reacted in the presence of platinum. Additional amounts of the alpha-olefin fraction can be added following the first step. In the second step, the unsaturated ethylene oxide polymer is added and reacted. Additional amounts of the alpha-olefin fraction can be added following the second step. The reaction is carried out at temperatures in the range of 95° to 130° C. While chloroplatinic acid is the preferred catalyst, any suitable platinum containing catalyst may be employed. Upon cooling, the wax reaction product can be used in the preparation of organic emulsifier free water-in-oil emulsions.

These emulsions are formed from an oil phase and a water phase. Neither phase contains an organic emulsifying agent. The oil phase contains the water dispersible silicone wax and one or more organic emollient oils. An electrolyte in the water phase may be required for purposes of stabilization. Mixing, stirring, agitation, or homogenization, of the two phases yields a stable organic emulsifier free water-in-oil emulsion.

A distinct advantage and benefit of the invention is that it enables one skilled in the art, by a simple means, to formulate high viscosity emulsions, without the need of complex equipment for reducing particle size, or expensive thickening and gelling agents. Thus, water-in-oil emulsions having a viscosity in excess of about 100,000 centistokes can be produced, and more preferably, emulsions having a viscosity in excess of about 150,000 centistokes. Water-in-oil emulsions most preferred according to the present invention have a viscosity in the range of about 150,000 centistokes to about 200,000 centistokes or more.

Water-in-oil emulsions prepared according to the present invention contain from 5 to 50 percent by weight of one or more organic oils as an emollient, from 44 to 94.5 percent by weight of water, from zero up to about one percent by weight of an emulsion stabilizer which can be an electrolyte such as sodium chloride or ammonium chloride, and from 0.5 to 5 percent by weight of the water dispersible silicone wax.

Emollient oils which can be employed in the present invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; and hydrocarbons such as petrolatum and squalane.

Water-in-oil emulsions prepared according to the present invention are free of organic emulsifiers such as anionic, cationic, and nonionic, surface active agents. Instead, the water dispersible silicone wax of this invention performs the function of holding together and compatibilizing the two otherwise immiscible phases. This is another distinct advantage and benefit of these emulsions when applied to consumer goods, since the presence of an organic emulsifying agent in a personal care product can often be responsible for potential skin irritation.

The following examples are set forth for the purpose of illustrating the invention in more detail.

EXAMPLE I

A mixture of 15.7 grams of a linear polymethylsiloxane having a molecular weight of about 3600 and containing 0.25 equivalents of Si-H; 4.22 grams (0.008 mole) of a C30+ olefin fraction; and 0.02 grams (1 ppm Pt) of a one percent solution of $H_2PtCl_6$ in isopropanol; was heated to ninety-five degrees Centigrade. The mixture exothermed to 105° C. After five minutes, 86.15 grams (0.16 mole) of a C30+ olefin fraction was added over a period of forty-five minutes accompanied by heating at 110°-120° C. To the mixture was added nine grams of isostearyl alcohol as a compatibilizer; followed by the addition of 11.67 grams (0.012 mole) of an allyl-initiated polyethylene glycol having a molecular weight of 938 and the formula $H_2C=CH-CH_2-O-(CH_2CH_2O)_{20}H$; and 0.10 grams (4 ppm Pt) of a one percent solution of $H_2PtCl_6$ in isopropanol. The temperature was raised to 130° C. and the mixture was heated for thirty minutes. The final step in the synthesis was the addition of 37.63 grams (0.07 mole) of a C30+ olefin fraction followed by heating at 130° C. for one hour. Upon cooling, a product was recovered which was a white wax having a softening point of 72°-75° C. Reheating of the product above its softening point produced a clear very viscous fluid. Residual Si-H in the product was analyzed to be 130 ppm.

EXAMPLE II

A water-in-oil emulsion was prepared as follows. First, an oil phase was formed by combining nineteen percent by weight of mineral oil, six percent by weight of sunflower oil, and two percent by weight of the white wax product from Example I. The mineral oil, sunflower oil, and the white wax product from Example I, were mixed together and heated to 75° C. to melt the wax. A water phase was then formed with seventy-two percent by weight of deionized water containing one percent by weight of sodium chloride as a stabilizing agent for the emulsion. The water phase was mixed and heated to 75° C. The water phase was added to the oil phase very slowly and the two phases were mixed until uniform. The mixture was cooled to room temperature. The resulting product was a white thick oil-in-water emulsion having a "fluffy" texture and a pH of 6.7. The viscosity of the emulsion was 190,000 centistokes as determined with an RVT-D viscometer rotating at 2.5 rpm for sixty seconds.

EXAMPLE III

The emulsion in Example II was evaluated and found to be an effective skin conditioner, in maintenance of skin smoothness, softness, and protection of the skin from dryness. When applied to the skin, the emulsion had a dry smooth feel. Other variations and modifications may be made in the compounds, compositions, and methods described herein without departing from the essential features and concepts of the present invention.

The forms of the invention described herein are exemplary only and are not intended as limitations on the scope of the invention as defined in the appended claims.

That which is claimed is:

1. A method of softening skin comprising applying to the skin a water-in-oil emulsion which includes 5 to 50 percent by weight of an organic oil; 44 to 94.5 percent by weight of water; and 0.5 to 5 percent by weight of a water dispersible silicone wax; the water dispersible silicone being derived from the reaction of (i) an $\equiv$SiH containing siloxane having a formula selected from the group consisting of $Me_3SiO(MeHSiO)_xSiMe_3$ and $Me_3SiO(MeHSiO)_x(Me_2SiO)_ySiMe_3$ in which Me is the methyl radical, and x and y are integers, the value of the integer x being from twenty to one hundred, and the value of the integer y being from one to one hundred, with the proviso that the ratio of x/y is at least two or more; (ii) a linear C30+ organic alpha-olefin; and (iii) an unsaturated ethylene oxide polymer having the formula $H_2C=CH-CH_2-O(CH_2CH_2O)_zH$ in which z has a value of at least sixteen; the emulsion being free of organic emulsifying agents.

2. A method according to claim 1 in which the emulsion has a viscosity in excess of about 100,000 centistokes.

3. A method according to claim 1 in which the emulsion has a viscosity in excess of about 150,000 centistokes.

4. A method according to claim 1 in which the emulsion has a viscosity in the range of about 150,000 centistokes to about 200,000 centistokes.

5. A method according to claim 1 in which the organic oil is present in the form of a mixture of two different organic oils.

6. A method according to claim 1 in which the emulsion includes up to about one percent by weight of an emulsion stabilizer in the form of an electrolyte selected from the group consisting of sodium chloride and ammonium chloride.

* * * * *